US00PP09968P

United States Patent [19]

Jessel, Jr. et al.

[11] Patent Number: Plant 9,968

[45] Date of Patent: Jul. 15, 1997

[54] CARNATION PLANT VARIETY NAMED 'CFPC RURI'

[75] Inventors: Walter H. Jessel, Jr., Gonzales; Richard Shido, Salinas, both of Calif.

[73] Assignee: California Florida Plant Co., L.P., Salinas, Calif.

[21] Appl. No.: 627,375

[22] Filed: Apr. 4, 1996

[51] Int. Cl.[6] ..... A01H 5/00

[52] U.S. Cl. ..... Plt./73.2

[58] Field of Search ..... Plt./73.2

*Primary Examiner*—Howard J. Locker

*Attorney, Agent, or Firm*—Christie, Parker & Hale, LLP

[57] ABSTRACT

A new variety of carnation plant producing white flowers and very resistant to *F. oxysporum*.

1 Drawing Sheet

SUMMARY OF THE INVENTION

The present invention relates to a new and distinct variety of carnation plant which was discovered as a sport in a controlled planting of the cultivar 'Loniatex', also known as "President", and commercially available as a lavender-flush colored carnation of the 'Vanessa' family. The varietal denomination of this new carnation is 'CFPC Ruri'.

Among the novel combination of characteristics possessed by the new variety which distinguishes it are superior resistance to *F. oxysporum*, strains 1 and 2, and white flowers with a clove-like fragrance. The new variety differs from its parent in flower coloration since 'CFPC Ruri' produces white, not lavender-flush flowers.

Asexual reproduction by propagation by side shoot cuttings of the new variety as performed in Salinas, Calif., shows that the foregoing and other distinguishing characteristics come true to form and are established and transmitted through succeeding propagations.

BRIEF DESCRIPTION OF ILLUSTRATION

The accompanying illustration shows a typical specimen of the flowers of the new variety depicted in color as nearly true as it is reasonably possible to make the same in color illustration of this character.

DESCRIPTION OF THE NEW VARIETY

The following is a detailed description of my new variety, with color terminology in accordance with The Royal Horticultural Society Color Chart (R.H.S.C.C.). The terminology used in color description herein refers to plate numbers in the aforementioned color chart. Color designations and color descriptions may deviate from the stated values depending upon varying environmental, seasonal and cultural conditions.

The information provided herein is based on observations of plants grown inside commercial greenhouses at Salinas, Calif. The height of plant and flower and foliage size are established as an average using standard commercial cultural practices. Where terms such as average, normal, ordinary, etc., are used, the characteristics so described are not considered distinguishing.

Name: 'CFPC Ruri'.

Classification:

*Botanical.*—Hybrid, *Dianthus caryophyllus.*

*Commercial.*—Carnation, standard disbud type.

Parentage: Sport of 'President', a lavender frosted colored carnation of the 'Vanessa' family.

1. Plant:
   - *Height.*—About 38 inches (first flowering).
   - *Growing habit.*—Herbaceous, semi-upright.
   - *Blooming habit.*—As a standard.
   - *Blooming season.*—Year round.
   - *Rooting Time.*—About 15 days.
   - *Mutation prone.*—No.
   - *Disease resistance.*—Very good.
   - *Temperature tolerance.*—Wide range.
   - *Breaking action.*—Good, about 5 on average.
2. Foliage:
   - *Color.*—Upper side: Near 132A. Lower side: Near 132B.
   - *Size.*—About 5⅝ inches long, about ⅜ inches wide.
   - *Quantity.*—Numerous.
   - *Shape.*—Lanceolate.
   - *Texture.*—Smooth.
   - *Ribs.*—Central, keeled.
   - *Arrangement.*—Bi-lateral along stem.
   - *Stem color.*—Dark green.
3. Bud:
   - *Shape.*—Ovoid
   - *Color.*—Light green.
   - *Length.*—About 1¼ inches.
   - *Diameter.*—About ½ inch.
4. Calyx:
   - *Number of sepals.*—About 5.
   - *Length.*—About ¼ inch.
   - *Width.*—About ⅓ inch.
   - *Color.*—Outside — Dark green. Inside — Light green.
5. Bloom:
   - *Shape.*—Round.
   - *Size.*—Diameter average: About 3¾ inches. Depth average: About 1½ inches.
   - *Borne.*—Terminally as a disbud.
   - *Color.*—General tonality: White. Upper side: Whiter than 155D. Lower side: Whiter than 155D. Center: Whiter than 155D. Outer petals: Whiter than 155D.
   - *Keeping quality.*—2½ to 3 weeks.
   - *Fragrance.*—Very strong.
6. Petals:
   - *Number.*—About 48.
   - *Outer petals.*—Length: About 2 inches. Width: About 1⅜ inches.
   - *Central petals.*—Length: About 1⅝ inches. Width: About ⅝ inch.
   - *Texture.*—Smooth.
   - *Form.*—Fan shaped.
   - *Appearance.*—Shiny.
7. Reproductive organs:
   - *Stamens.*—About 5.

*Anthers.*—About ⅛ inch, near 155D.
*Filaments.*—About ⅞ inch, white.
*Pistil.*—Number: About 1. Color: White. Length: About ¼ inch.
*Stigma.*—Number: About 2. Color: White.
*Overy.*—Shape: Conical. Color: Base — white. Body — green. Apex — tan.

*Fertility.*—Female: Poor. Male: Very poor.

We claim:

1. A new and distinct variety of carnation plant substantially as shown ad described.

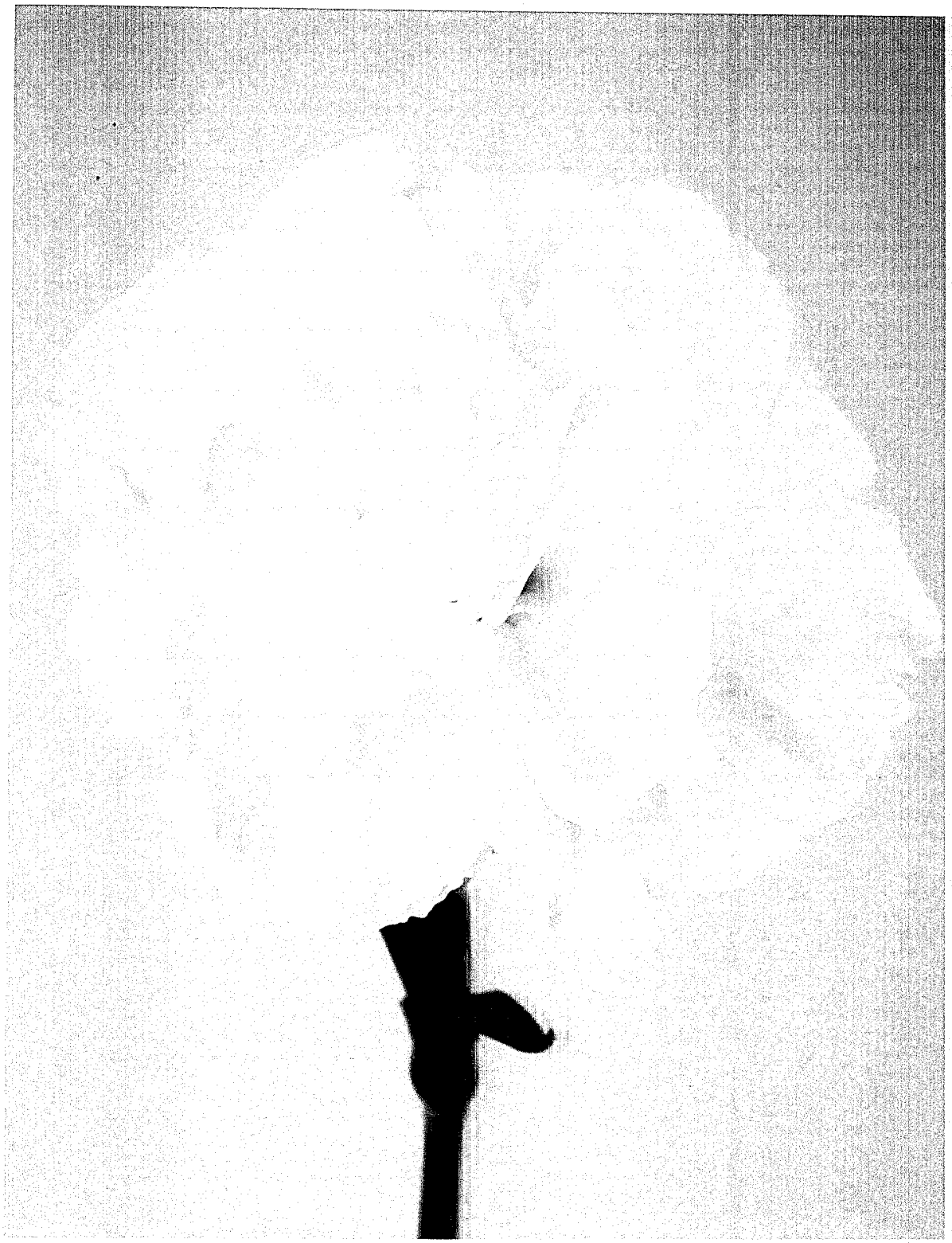

* * * * *